US010543388B2

(12) United States Patent
Rachele (10) Patent No.: US 10,543,388 B2
(45) Date of Patent: Jan. 28, 2020

(54) EXERCISE SYSTEMS INCLUDING WEIGHT CLUSTERS COMPOSED OF WEIGHT PODS, AND COMPONENTS OF SUCH SYSTEMS

(71) Applicant: Clustas, LLC, Peru, VT (US)

(72) Inventor: Rollin Rachele, Peru, VT (US)

(73) Assignee: Clustas, LLC, Peru, VT (US)

( * ) Notice: Subject to any disclaimer, the term of this patent is extended or adjusted under 35 U.S.C. 154(b) by 113 days.

(21) Appl. No.: 15/738,965

(22) PCT Filed: Jul. 22, 2016

(86) PCT No.: PCT/US2016/043579
§ 371 (c)(1),
(2) Date: Dec. 21, 2017

(87) PCT Pub. No.: WO2017/019512
PCT Pub. Date: Feb. 2, 2017

(65) Prior Publication Data
US 2018/0169456 A1   Jun. 21, 2018

(30) Foreign Application Priority Data

Jul. 24, 2015   (GB) .................................. 1513076.8

(51) Int. Cl.
*A63B 21/00*   (2006.01)
*A63B 65/06*   (2006.01)
(Continued)

(52) U.S. Cl.
CPC .... *A63B 21/00065* (2013.01); *A63B 21/0603* (2013.01); *A63B 21/065* (2013.01);
(Continued)

(58) Field of Classification Search
CPC .......... A63B 21/06–08; A63B 21/0603; A63B 21/0065; A63B 21/0605; A63B 21/0607
See application file for complete search history.

(56) References Cited

U.S. PATENT DOCUMENTS 1,524,888 A * 2/1925 Schuur ............... A63B 21/0605
482/108
1,577,077 A * 3/1926 Huston ................ A63B 21/065
482/105

(Continued)

OTHER PUBLICATIONS

International Search Report and Written Opinion dated Oct. 6, 2016 in connection with PCT/US16/43579.

*Primary Examiner* — Nyca T Nguyen
(74) *Attorney, Agent, or Firm* — Downs Rachlin Martin PLLC (57) ABSTRACT

Exercise systems that include self-coupling weight pods that couple with one another to form weight clusters that a user can use in performing various body movements, such as exercise and conditioning movements. Each weight pod typically has a calibrated weight so that the user may know the amount of weight they are using. Each weight pod includes one or more coupling features that allow that weight pod to couple to one or more other weight pods and/or to an accessory, such as a strap. In some embodiments, each weight pod is soft so as to inhibit injury to a user of another close by the user. The weight pods can be used with one or more accessories, such as a strap, a bell bag that emulates a kettle bell, and a rucksack that can be configured to be a multifunctional component of an overall exercise system, among others.

24 Claims, 8 Drawing Sheets

(51) Int. Cl.
*A63B 21/06* (2006.01)
*A63B 21/065* (2006.01)
*A63B 21/072* (2006.01)

(52) U.S. Cl.
CPC ...... *A63B 21/0722* (2015.10); *A63B 21/4005* (2015.10); *A63B 21/4009* (2015.10); *A63B 21/4019* (2015.10); *A63B 21/4029* (2015.10); *A63B 21/4035* (2015.10); *A63B 65/06* (2013.01); *A63B 2209/08* (2013.01); *A63B 2225/09* (2013.01)

(56) References Cited

U.S. PATENT DOCUMENTS

| | | | | |
|---|---|---|---|---|
| 2,569,833 | A | | 10/1951 | Simpson |
| 3,463,486 | A | * | 8/1969 | James, Jr. ......... A63B 21/0604 482/106 |
| 4,984,784 | A | * | 1/1991 | Bailey ............... A63B 23/16 482/44 |
| 5,058,885 | A | * | 10/1991 | Brant ................ A63B 21/0603 473/596 |
| 5,242,348 | A | * | 9/1993 | Bates ................ A63B 21/0004 482/105 |
| 6,216,926 | B1 | * | 4/2001 | Pratt ................ A45F 3/04 224/148.2 |
| 6,217,504 | B1 | * | 4/2001 | Phillips ............. A61N 2/004 600/9 |
| 6,244,997 | B1 | * | 6/2001 | Cook ................ A63B 21/065 482/105 |
| 6,652,421 | B1 | * | 11/2003 | Chen ................ A63B 21/0603 482/49 |
| 7,494,451 | B1 | * | 2/2009 | Ramos .............. A63B 21/0728 482/107 |
| 2005/0227830 | A1 | * | 10/2005 | Tomlin .............. A41D 19/0024 482/105 |
| 2006/0027022 | A1 | | 2/2006 | Flora et al. |
| 2008/0200090 | A1 | * | 8/2008 | Balanchi ............ A63H 33/046 446/92 |
| 2010/0022361 | A1 | * | 1/2010 | Raines ............... A63B 21/06 482/93 |
| 2010/0048363 | A1 | * | 2/2010 | Gilberti ............. A63B 21/0603 482/105 |
| 2010/0075816 | A1 | * | 3/2010 | Anderson .......... A63B 21/0728 482/107 |
| 2010/0298099 | A1 | * | 11/2010 | Wierszewski ......... A63B 21/06 482/44 |
| 2011/0009713 | A1 | * | 1/2011 | Feinberg ............. A61B 5/0205 600/301 |
| 2011/0082017 | A1 | * | 4/2011 | Arlie ................ A63B 21/0601 482/108 |
| 2011/0172621 | A1 | | 7/2011 | Lee et al. |
| 2012/0046148 | A1 | * | 2/2012 | Aguila ............... A63B 21/072 482/93 |
| 2012/0149536 | A1 | * | 6/2012 | Trimble ............. A63B 21/00065 482/93 |
| 2012/0309593 | A1 | * | 12/2012 | Smith ................ A63B 23/16 482/49 |
| 2013/0157815 | A1 | * | 6/2013 | Reynolds ........... A63B 21/072 482/93 |
| 2013/0303342 | A1 | * | 11/2013 | Mandell ............. A63B 71/0054 482/105 |
| 2013/0310717 | A1 | * | 11/2013 | Ranky ............... G05G 9/04 601/40 |
| 2014/0011643 | A1 | * | 1/2014 | Jaidar ................ A63B 21/072 482/93 |
| 2014/0309090 | A1 | * | 10/2014 | Mandell ............. A63B 71/0054 482/105 |
| 2015/0051053 | A1 | * | 2/2015 | Conen ............... A63B 21/0602 482/108 |
| 2015/0196792 | A1 | * | 7/2015 | Towley .............. A63B 21/075 482/93 |
| 2015/0202486 | A1 | * | 7/2015 | Childs ............... A63B 21/075 482/106 |
| 2015/0343256 | A1 | * | 12/2015 | Coompol ........... A63B 21/0724 482/93 |
| 2016/0081489 | A1 | * | 3/2016 | Krass ................ A47D 13/02 224/158 |
| 2016/0129292 | A1 | * | 5/2016 | Stroup .............. A63B 21/00065 482/93 |

\* cited by examiner

FIG. 9C

EXERCISE SYSTEMS INCLUDING WEIGHT CLUSTERS COMPOSED OF WEIGHT PODS, AND COMPONENTS OF SUCH SYSTEMS

RELATED APPLICATION DATA

This application claims the benefit of priority of Great Britain Patent Application No. 1513076.8, filed on Jul. 24, 2015, and titled "A soft modular fitness device," which is incorporated by reference herein in its entirety.

FIELD OF THE INVENTION

The present invention generally relates to the field of exercise equipment. In particular, the present invention is directed to exercise systems including weight clusters composed of weight pods, and components of such systems.

BACKGROUND

Fitness devices, such as dumbbells, kettlebells, medicine balls, and sandbags, are common parts of gyms, and many people use them in their homes. Dumbbells, bar bells, and kettlebells tend to be heavy chunks of metal with a handle or bar and come in sets of fixed weights to meet the needs of a diverse public using them and for a diverse set of exercises targeting specific muscle groups. These devices in this form have been used for many years and are still used today. A more recent addition has been softer weights, such as sandbags and medicine balls, that offer a different array of potential exercises.

SUMMARY OF THE DISCLOSURE

In one implementation, the present disclosure is directed to an exercise system that includes a plurality of self-coupling weight pods designed and configured to form a weight cluster of known mass, each self-coupling weight pod having a calibrated mass selected to contribute to the known mass of the weight cluster, and including at least one coupling feature designed and configured to allow the self-coupling weight pod to be coupled to a plurality of other ones of the plurality of self-coupling weight pods to form the weight cluster.

In another implementation, the present disclosure is directed to an exercise device that includes a shell made of non-ferromagnetic material, the shell providing a chamber and a flexible envelope having an exterior surface, a ferromagnetic material contained within the chamber, and at least one magnet located so as to attract the exercise device to a ferromagnetic body located externally to the exercise device.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

In some aspects, the present invention is directed to exercise systems that include self-coupling weight pods configured to be coupled with one another so as to form one or more weight pods that an exerciser can use to perform any one or more of a variety of fitness exercises, including aerobic exercises such as jumping jacks, walking, and jogging, among others, anaerobic exercises such as curls, arm extensions and bend overs, among others, and/or can use in other activities, such as playing catch and juggling, among others The user may use each weight cluster as is or with one or more accessory components, such as a torso belt, a hand strap, an arm/leg strap, a bell bag, a rucksack, a handle, and/or a bar, among others. In some embodiments, such as embodiments including a handle, a bar, a belt, or a strap, each of such accessories may be designed and/or configured to allow the weight pods to individually couple to the accessory and/or couple to the accessory in one or more weight clusters. Examples of some of these accessories are illustrated in FIGS. 6A to 9C and described below.

Figure 1:
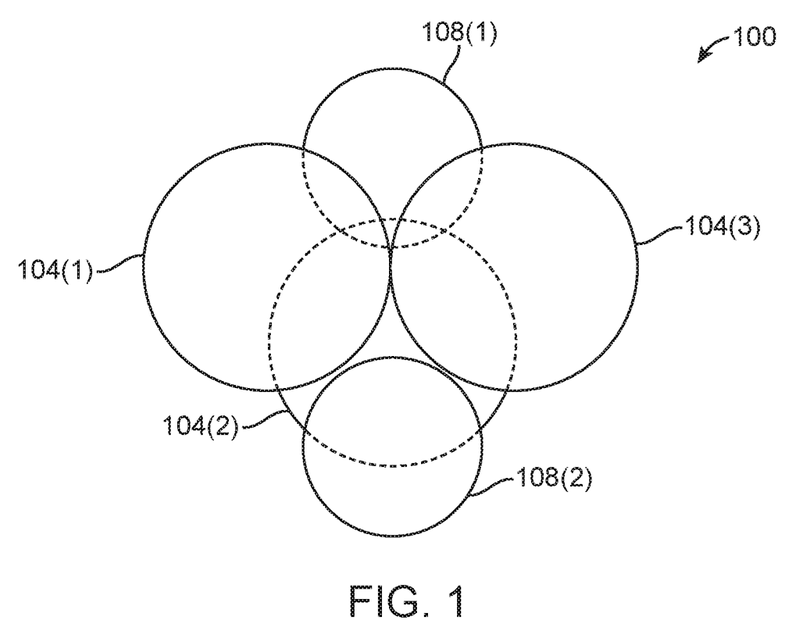
FIG. 1 is a view of a weight cluster of self-coupling weight pods made in accordance with aspects of the present invention.
Figure 2:
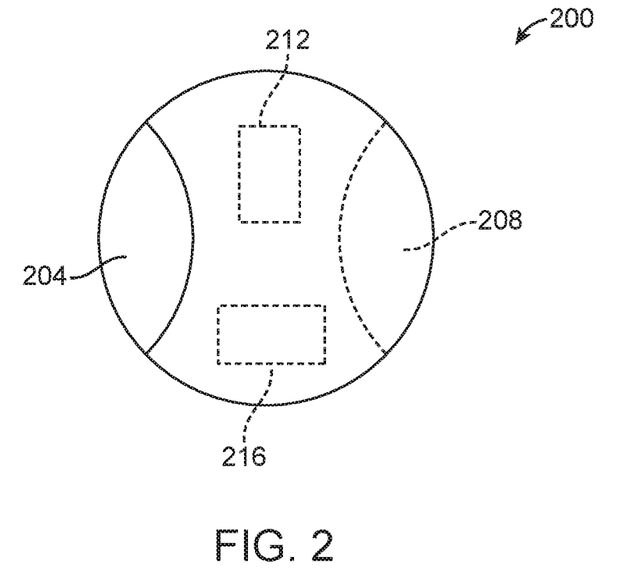
FIG. 2 is a partial exterior view/partial diagrammatic view of a self-coupling weight pod designed and configured for use in a weight cluster, such as the weight cluster of FIG. 1.

Referring now to the drawings, FIG. 1 illustrates an exemplary weight cluster 100 composed of a plurality of self-coupling weight pods, here a set of three relatively larger self-coupling weight pods 104(1) to 104(3) and a pair of relatively smaller self-coupling weight pods 108(1) and 108(2). FIG. 2, shows a self-coupling weight pod 200 to illustrate a variety of aspects and features that the self-coupling weight pod includes or may include, depending on the desired configuration and/or application for a particular embodiment. Self-coupling weight pod 200 may be viewed as generally representing aspects and features of any of the self-coupling weight pods shown and described herein, including self-coupling weight pods 104(1) to 104(3), 108(1), and 108(2) of weight cluster 100 of FIG. 1 and self-coupling weight pods 300, 400, and 500 of FIGS. 3-5, among others. Following are descriptions of some of the aspects and features that self-coupling weight pod 200 may include.

Self-coupling weight pod 200 may be any suitable fundamental shape, such as spherical, polyhedron, ovoid, prismatic, tubular, shaped to mimic an animal, plant, building, etc., among others. Fundamentally, there is no limitation on the shape of a self-coupling weight pod made in accordance with the present disclosure. By "fundamental shape" it is meant the shape intended by the designer, and this term is used to account for the fact that, when a self-coupling weight pod is made to be soft, the shape of a self-coupling weight pod may change due to its pliability. Regarding softness, the softness, or pliability, of each self-coupling weight pod so configured can be adjusted to suit various conditions, such as the weight and/or density of the material(s) used to construct the weight pod and the desired level of pliability. The level of pliability, in turn, may be selected based on any one or more factors, such as intended use (e.g., as a weight and for squeezing, for throwing, kneading, etc.) and to accommodate the coupling features (see, e.g., FIGS. 3-5 and accompanying descriptions), among others.

The desired softness and pliability can be effected in a variety of ways. For example, if a self-coupling weight pod, such as self-coupling weight pod 200, comprises a shell and a separate fill contained in the shell, the shell may be made of one or more suitable rigid or pliable materials, such as a polymer, woven or nonwoven fabric (elastic or non-elastic), flexible composite, chain mail, and foam, among others, and any suitable combination thereof. As those skilled in the art will appreciate, the fundamental shape(s), the deformed shape(s), and the type(s) and configuration(s) of the coupling feature(s) of each self-coupling weight pod can dictate how the self-coupling weight pods can be clustered together to form a self-coupled weight cluster, such as weight cluster 100 of FIG. 1. It is noted that for any given set of self-coupling weight pods, the self-coupling weight pods may be of the same shape or of differing shapes. As an example of differing shapes, two or more shapes may be selected so that, when coupled with one another to form a weight cluster, the self-coupling weight pods form a more compact weight cluster than would otherwise be formed if all of the self-coupling weight pods had the same shape.

Self-coupling weight pod 200 of FIG. 2 may have any suitable size. For examples, in some embodiments in which the self-coupling weight pods are fundamentally spherical and filled with a relative dense material, such as iron shot, steel shot or ball bearings, each weight pod may have an outside diameter in a range of about 1 inch (~2.54 cm) to about 4 inches (~10.2 cm). Other shapes may have dimensions in the same or different size regime depending on the density of the primary mass-providing material(s) used. Those skilled in the art will readily appreciate how to select suitable dimensions based on the relevant design parameters, such as intended use, density of primary mass-providing material(s), pod shape, manner of coupling, and manner of clustering, among others. Generally, when shot is used, each piece of shot may have a diameter of about 0.25 inch (~0.64 cm). In some embodiments of self-coupling weight pod sets, the self-coupling weight pods in each set may all have the same size, whereas in other embodiments each set of self-coupling weight pods may contain self-coupling weight pods of differing sizes. For example, each relatively larger self-coupling weight pod may have a weight (mass) that is larger than each relatively smaller self-coupling weight pod. As an example of a set of differing size self-coupling weight pods, the set may have two different sizes, with the larger self-coupling weight pods being 1 kg each and the smaller self-coupling weight pods being 0.5 kg each. In embodiments in which a set of self-coupling weight pods have the same dimensional size, the set may include self-coupling weight pods of differing weights. The differing weights may be effected by varying the composition of the self-coupling weight pods and/or varying the amount of weighting material provided to the self-coupling weight pods. Each self-coupling weight pod may be optionally marked with one or more indicia that indicate the weight (mass) of that self-coupling weight pod.

Self-coupling weight pod 200 of FIG. 2 will typically, but not necessarily, have a calibrated known mass that is a convenient value in terms of magnitude, so that a user does not have to use too many self-coupling weight pods or is not faced with increments that are too large, and in terms of summing together the weights of multiple self-coupling weight pods when used together, such as in weight clusters. Examples of such convenient values include 0.5 kg, 1 kg, 2 kg for metric self-coupling weight pods and 1 lb, 2 lb, and 4 lb for avoirdupois self-coupling weight pods. Of course, other values, including not so convenient values, can be used, especially if knowing the precise weights of a weight cluster formed therewith is not important. Regarding the terms "weight" and "mass" as used herein, these terms are used interchangeably as appears customary in the field of fitness devices.

Self-coupling weight pod 200 of FIG. 2 includes one or more coupling features, such as coupling features 204 and 208, that allow the self-coupling weight pod to be readily and firmly coupled to another self-coupling weight pod and/or each of one or more accessories, such as a belt, strap, bar, handle, etc., and to readily be repeatedly decoupled and recoupled, for example, to provide easily reconfigurable weight clusters when desired by a user. Each coupling feature is typically a component of a pair of complementary coupling features that effect the coupling. For example, in some embodiments the coupling may be a magnetic coupling such that the complementary coupling features include a pair of magnets located on a pair of self-coupling weight pods and arranged to be attracted to one another or include one or more magnets on one self-coupling weight pod and a ferromagnetic material in another self-coupling weight pod such that the magnet(s) of one self-coupling weight pod is(are) attracted to the ferromagnetic material of the other self-coupling weight pod. The exemplary self-coupling weight pods 300, 400, and 500 of FIGS. 3-5, described below in detail, illustrate an exemplary arrangement of complementary coupling features that provide magnetic coupling.

As another example, in some embodiments the coupling may be a mechanical coupling effected by a suitable mechanical fastener having complementary interlocking components, such as hook-and-loop fastener components, such as VELCRO® fastener components, or interlocking-island fastener components, such as LYNX™ interlocking-island fastener components, the former being available from Velcro USA Inc., Manchester, N.H., and the latter being available from Chittenden Research and Development, LLC, Hinesburg, Vt. In the case of mechanical fasteners having differing complementary components, such as a hook component and a loop component, a particular self-coupling weight pod in a set may have only one component (e.g., the hook component) or both components. When a self-coupling weight pod has only one component, the entire exterior of that self-coupling weight pod may be covered with that component. Alternatively, the component may be provided on one or more discrete regions, bands, etc. When a self-coupling weight pod has both complementary components, they may be located and arranged in any manner that provides sufficient coupling "power" to hold the self-coupling weight pod firmly to the one or more other self-coupling weight pods and/or accessory to which it is coupled. Examples of other coupling features include, but are not limited to, pouches, suction cups, tentacles, or any other means for achieving the same result, and any suitable combination thereof. It is noted that depending on the nature of a particular coupling feature, the coupling feature may be located either on the exterior or the interior of a self-coupling weight pod (e.g., in the case of a magnet and a ferromagnetic material) or only on the exterior of the self-coupling weight pod (e.g., in the case of hook-and-loop and interlocking-island fasteners, and a suction cup).

A self-coupling weight pod of the present disclosure, such as self-coupling weight pod 200 of FIG. 2, can be enhanced in any one or more of a variety of ways. For example, self-coupling weight pod 200 can optionally contain electronics 212 and/or have one or more attachments 216. Examples of types of electronics that can be used for the one or more electronics 212 include electronics that measure heart rate variability, pulse, skin resistance, number of squeezes, repetitions of movement, changes in force or inertia, length of time in use, or any function derived from these, among other measurements, and electronics that provide other functions, such as light, sound, haptic feedback, and any combination of such measurement and other functions. Examples of attachments that can be used for the one or more attachments 216 include attachments that enhance the usefulness and/or user experience, such as decoration, visual effect, strings, bungees, elastic strips, whistles, envelopes, wrappers, elongations, handles, grips, gloves, logos, stickers, hooks, etc., and any combination thereof.

Figure 3:
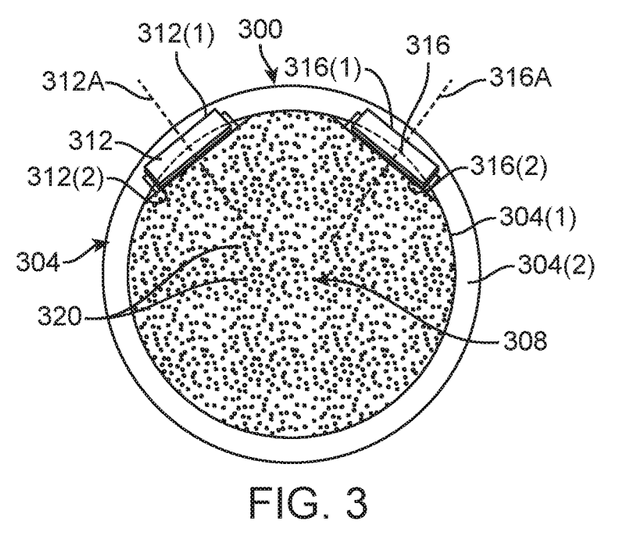
FIG. 3 is a cross-sectional view of a magnet-based self-coupling weight pod made in accordance with aspects of the present disclosure.

With various aspects of features of an exercise system of the present disclosure described generally above, attention is now directed to FIG. 3, which illustrates a particular self-coupling weight pod 300 having a configuration that is quite versatile. In this embodiment, self-coupling weight pod 300 includes a shell 304 and a fill 308 contained within the shell. Also in this particular embodiment, self-coupling weight pod 300 is magnetic-coupling based and includes two complementary magnetic coupling components, namely one or more magnets, here two magnets 312 and 316, providing the magnet attraction forces, and a ferromagnetic material 320, here acting also as fill 308, that is attracted to one or more magnets similar to magnets 312 and 316 on one or more other self-coupling weight pods, such as self-coupling weight pods 400 and 500 of FIGS. 4 and 5, and/or on an accessory, such as belt, strap, bar, or handle, among others. Each magnet 312 and 316 may be any suitable magnet, such as a neodymium magnet. In one particular example, each magnet 312 and 316 is an N35 neodymium magnet having a diameter of 20 mm and a thickness of 5 mm. Other types and/or other sizes of magnets can be used to suit design conditions.

Each magnet 312 and 316 includes a pair of opposite magnetic poles 312(1), 312(2), 316(1), and 316(2) spaced apart along a corresponding magnetic axis 312A and 316A. In the present embodiment, magnetic axes 312A and 316A are oriented so that like poles (north or south) face the same radial direction, either inward or outward. For example, both north poles of magnets 312 and 316 face either outward or inward. With this configuration, each magnet 312, 316 on self-coupling weight pod 300 will repel each magnet on a like self-coupling weight pod, such as each of self-coupling weight pods 400 and 500 of FIGS. 4 and 5, respectively, and only be attracted to the ferromagnetic material in the other self-coupling weight pod. The number, size, material, shape, and strength of the magnets provided to a self-coupling weight pod of the present disclosure, can vary, for example, to optimize the balance of attraction force depending on a multitude of variables, such as thickness and durability of the material(s) used for the shell, purity of ferromagnetic material, depth of the ferromagnetic material, weight and shape of the self-coupling weight pod, method of attaching the magnets to the self-coupling weight pod, the type and magnitude of forces that a weight cluster containing the self-coupling weight pod will encounter during use, and the manner in which a weight cluster can be handled by a user, among others. Those skilled in the art will readily understand the design parameters that need to be considered when designing a particular self-coupling weight pod or set of self-coupling weight pods.

In some embodiments, ferromagnetic material 320 is a flowable material such as a material consisting only of or otherwise containing iron shot, steel shot, steel ball bearings, or iron filings, among others, and any combination thereof. In some embodiments, ferromagnetic material 320 may include non-ferromagnetic material intermixed with or otherwise present with the components providing the ferromagnetism. When ferromagnetic material 320 is flowable and shell 304 is suitably pliable, self-coupling weight pod 300 may be quite malleable. For example, a user may quite readily be able to deform the fundamental spherical shape of self-coupling weight pod into another shape, such as a disc or egg-shape. The size, grade, shape, alloy, or any other aspect or property of ferromagnetic material 320 can also be varied to elicit different end results.

It is noted that ferromagnetic material 320 does not necessarily need to be flowable. For example, ferromagnetic material 320 may be a solid and/or rigid mass, such as a solid mass of steel or iron. In such a case, shell 304 of self-coupling weight pod 300 may be suitably thick and/or soft to provide the desired level of safety. As another example of a non-flowable ferromagnetic material, the ferromagnetic material may be a flexible layer, such as a steel chain mail layer, surrounding a non-ferromagnetic core, which can be rigid, pliable, flowable, etc.

In the present embodiment, shell 304 includes two layers, an inner layer 304(1) that functions as a containment layer for fill 308, which in this case is flowable, and an outer layer 304(2) that holds the containment layer and the fill and provides a durable layer for repeated handling and use. Examples of materials for inner layer 304(1) include, but are not limited to, rubber, fabric, silicone, neoprene, and plastic, such as thermoplastic polyolefin, thermoplastic polyurethane, and polyurethane, among others. If fabric is used, the fabric can be made of impregnated or laminated fabric(s) and/or any specially woven fabric(s) that is waterproof to prevent fill 308 from being exposed to moisture. This can be important, for example, if ferromagnetic material 320 is prone to rusting. Examples of materials for outer layer 304(2) include, but are not limited to, materials the same as or similar to the materials listed above for inner layer 304(1). In some cases, outer layer 304(2) may be thicker than inner layer 304(1), but this need not be so. Depending on the material(s) used for outer layer 304(2), the outer layer may be stretchy or not stretchy, either sewn, glued, taped, fastened with hook-and-loop fastener, from any number of pieces to form any desired shape. It is noted that inner layer 304(1) can be eliminated if outer layer 304(2) can provide the function(s) that the inner layer 304(1) would typically provide.

Figure 4:
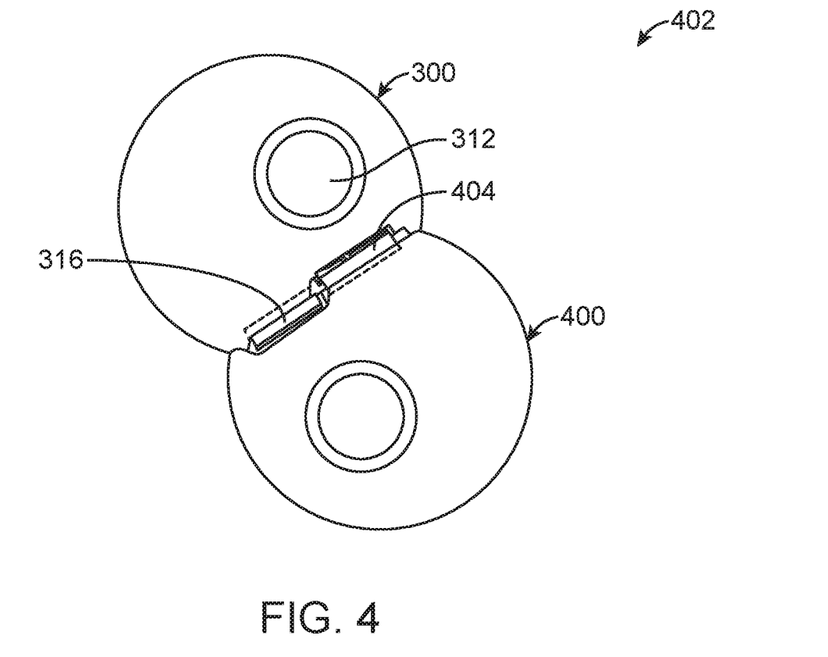
FIG. 4 is a reduced-size external view of two magnet-based self-coupling weight pods of FIG. 3 coupled together to form a weight cluster.
Figure 5:
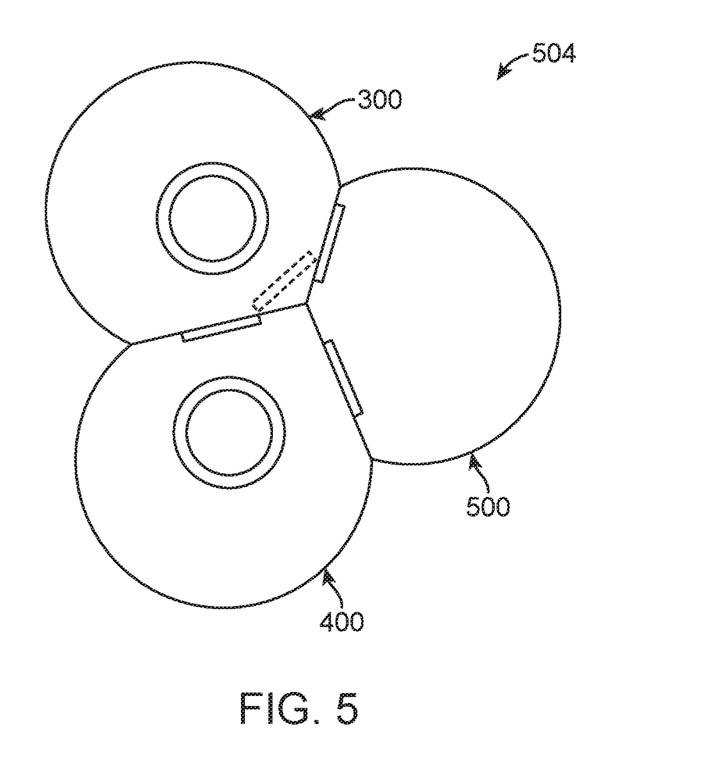
FIG. 5 is a reduced-size external view of three magnet-based self-coupling weight pods of FIG. 3 coupled together to form a weight cluster.

FIG. 4 illustrates self-coupling weight pod 300 of FIG. 3 coupled with like self-coupling weigh pod 400 to form a weight cluster 402. In this example, magnet 312 of self-coupling weight pod 300 is attracted to the ferromagnetic material (not seen) within self-coupling weight pod 400, and a like magnet 404 of self-coupling weight pod 400 is attracted to ferromagnetic material 308 (FIG. 3) within self-coupling weight pod 300. In this example, each of self-coupling weight pods 300 and 400 is soft and malleable, with the magnetic attraction between magnets 312 and 404 and the respective ferromagnetic materials of the opposing self-coupling weight pods is sufficient to deform each of the self-coupling weight pods from their fundamental spherical shape to the somewhat flattened shape shown in which the confronting portions of the self-coupling weight pods are flattened. FIG. 5 illustrates the addition of another instantiation 500 of magnetic-based self-coupling weight pod 300 to weight cluster 402 of FIG. 4 to form a larger and heavier weight cluster 504.

Figure 6A:
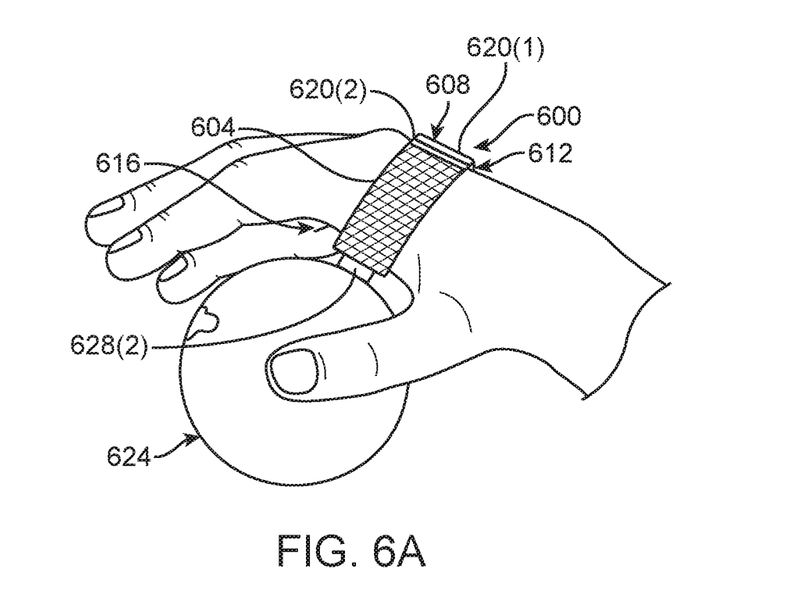
FIGS. 6A to 6C are various views of an exemplary strap for holding one or more weight pods and being engaged with a user's arm, leg, hand, etc., showing the strap engaged with a user's hand.
Figure 6B:
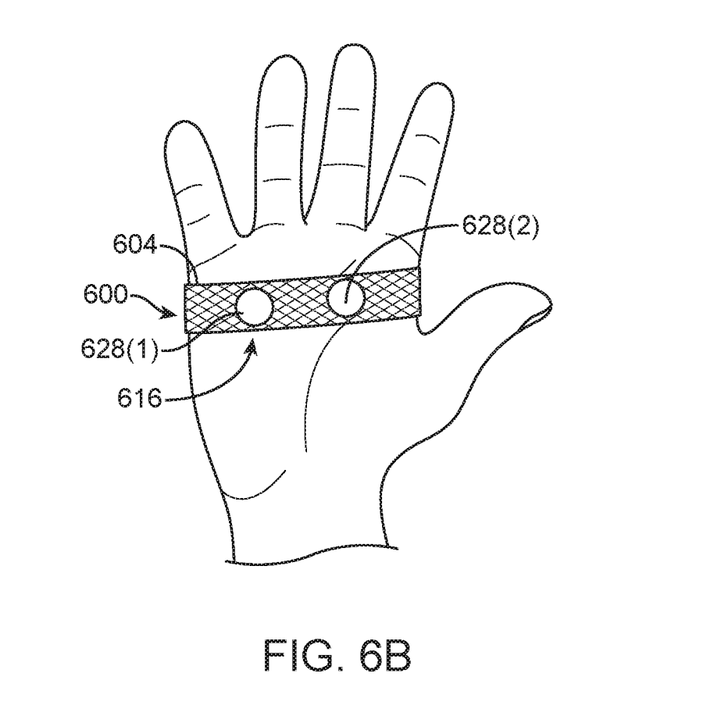
Figure 6C:
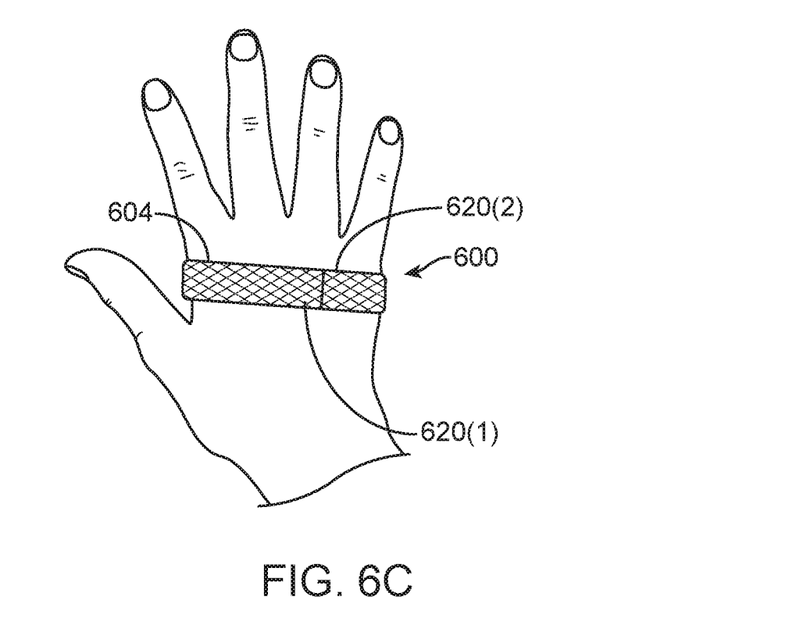

As mentioned above, individual and/or multiple ones of self-coupling weight pods made in accordance with the present invention, such as self-coupling weight pods 100, 300, 400, and 500 of FIGS. 1-5, may be used with any one or more accessories, such as a strap, bell bag, and rucksack, ferromagnetic dumbbells or kettlebells among others. FIGS. 6A to 6C show an example of an accessory strap 600 in the context of the strap being used as a hand strap. Those skilled in the art will appreciate, however, that strap 600, or a modified version thereof, may be used as another type of appendage strap, such as a leg strap, arm strap, ankle strap, wrist strap, etc. In this example, strap 600 includes a band 604, a length-adjustment mechanism 608, a fastening device 612, and a weight-pod coupling region 616. In the embodiment shown, length-adjustment mechanism 608 comprises two strap ends 620(1) and 620(2) that overlap one another, and fastening device 612 comprises complementary hook-and-loop fastening components (not seen, but located between the two strap ends) secured to corresponding respective ones of the strap ends. Other types of length-adjustment mechanisms and fastening devices can be used for other embodiments as desired. In addition, the strap may be rigid or stretchable but need not necessarily be adjustable. Also in the embodiment shown, weight-pod coupling region 616 is rigid or semi-rigid to provide a more stable structure for receiving one or more weight pods, such as self-coupling weight pod 624 shown. In this example, strap 600 includes a pair of magnets 628(1) and 628(2) (FIG. 6B) in weight-pod coupling region 616 for use with self-coupling weight pods configured for magnetic coupling, such as self-coupling weight pods 300, 400, and 500 of FIGS. 3-5, respectively. Stiffening weight-pod coupling region 616 can be beneficial when multiple magnets are used to keep the magnets from attracting to and encroaching on one another. Band 604 may be made of any one or more of any suitable materials, such as nylon webbing, leather, polymer, etc.

Figure 7:
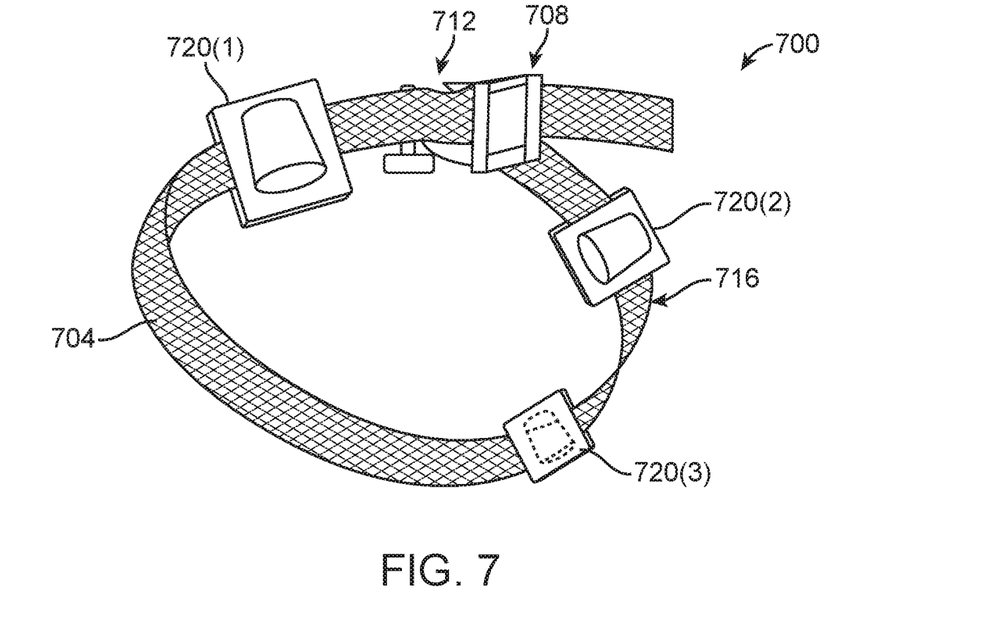
FIG. 7 is a view of another exemplary strap in the form of a torso belt that may be used to hold one or more weight pods, weight clusters, and/or one or more accessories.

FIG. 7 illustrates another exemplary accessory strap executed in the form of a belt 700. In this example, belt 700 includes a band 704, a length-adjustment mechanism 708, a fastening device 712, and a weight-pod receiving region 716. In the embodiment shown, length-adjustment mechanism 708 comprises a friction-type strap-length adjuster common on adjustable-length nylon webbing straps, and fastening device 712 comprises a polymer buckle. Other types of length-adjustment mechanisms and fastening devices can be used for other embodiments as desired. Also in this embodiment, weight-pod receiving region 716 is engaged by a plurality of holsters, here three removable holsters 720(1) to 720(3), here, cup-shaped holsters, each designed and configured to hold at least one self-coupling weight pod, a water bottle, and/or another accessory (not shown). Each holster 720(1) to 720(3) may be collapsible when not in use, and/or slid, repositioned, and/or unclipped. In some embodiments, weight-pod receiving region 716 can be provided with one or more coupling features, such as one or more magnets, one or more hook-and-loop fasteners, one or more interlocking island fasteners, snaps, straps, and integrated pouches, among others, to allow one or more self-coupling weight pods to be coupled to belt 700. The number, size, shape, and overall dimensions of each holster cup 720(1) to 720(3) can vary, and each can be rigid or semi-rigid or even just a stretchy fabric with or without fasteners to hold one or more weight pods, water bottle, or other object(s) in place. Band 704 may be made of any suitable stretchy or non-stretchy material or a combination of both, and may have any suitable fixed or varying width, for example, to give extra support during lifting or to simply provide enough width for comfortable support of the weight that belt 700 carries. Belt 700 can be a standalone belt or designed to be combined with another accessory, such as rucksack 900 of FIGS. 9A to 9C, for its weight-bearing positioning and properties. Belt 700 may come with or without a closeable pouch (not shown) to hold other items of interest such as a wallet, glasses, keys, gloves, padlock, or any other personal-use item. The pouch may come with any closing mechanism such as zipper, button, hook-and-loop fastener, etc.

Figure 8A:
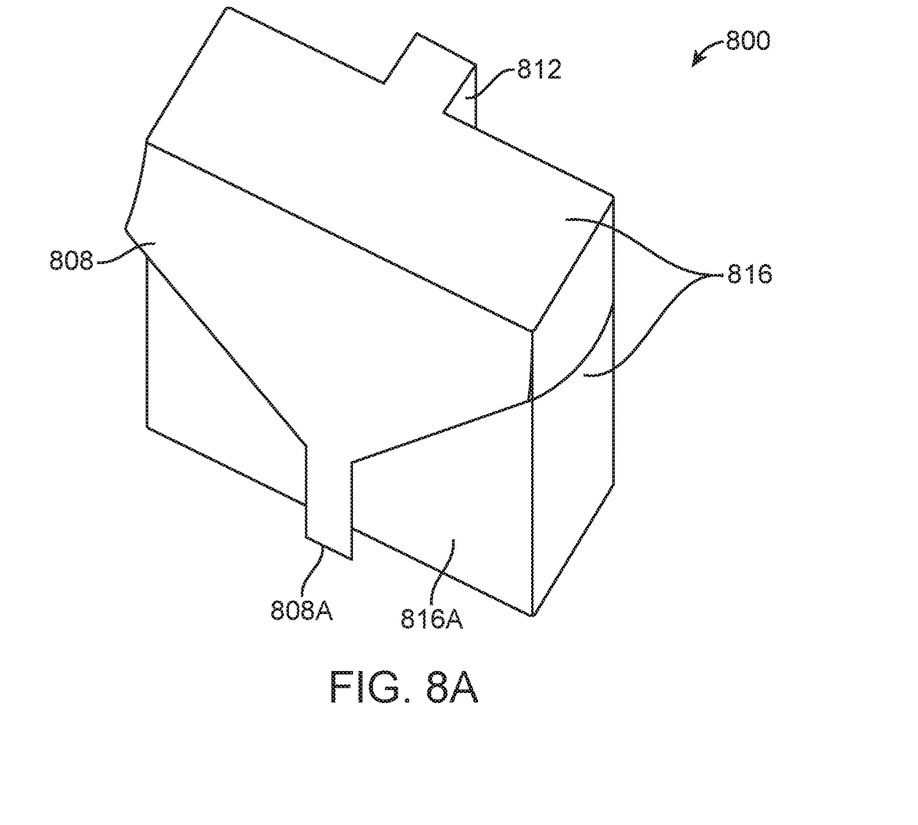
FIGS. 8A and 8B are various external views of an exemplary bell bag that may be used to hold a plurality of discrete weights to allow a user to use the weights, for example, for kettlebell-type exercises.
Figure 8B:
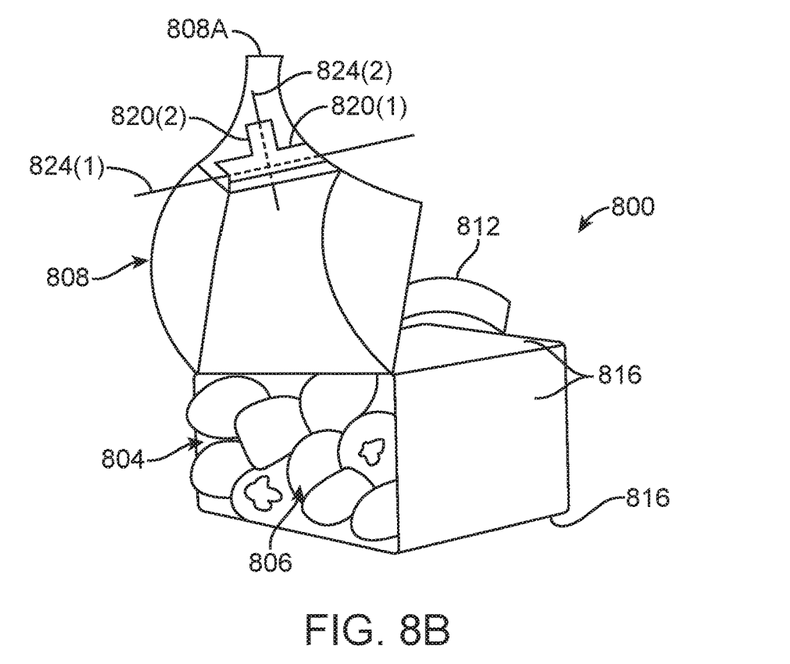

FIGS. 8A and 8B illustrate an exemplary accessory bell bag 800 that is designed and configured to allow a user to perform exercises and/or other body movements typically performed by exercise kettlebells well known in the art. In the present embodiment, bell bag 800 defines a weight-receiving compartment 804 (FIG. 8B) for receiving weights, such as a plurality of self-coupling weight pods 806 of the present disclosure, a closure 808 that securely closes the weight-receiving compartment and keeps the weight(s) therein during rigorous use of the bell bag, and a handle 812 that allows a user to hold the bell bag secured during use. Handle 812 may be a relatively large handle for uses similar to a kettlebell, and closure 808 may be quick opening to provide an advantage that the one size can be filled with the desired weight. Bell bag 800 may also be soft to make it safer than conventional metal kettlebells.

In the example shown, bell bag 800 has walls 816 that are semi-rigid and substantially hold the overall shape of the bell bag when fully loaded with weight and being used for conventional kettlebell-style exercises. Closure 808 in this example is provided on a sidewall of bell bag 800 and is likewise semi-rigid. Also in the example, closure 808 is removably secured in a closed position using complementary hook-and-loop fastener components, with two strips 820(1) and 820(2) oriented perpendicularly to one another on one, the other, or both of a flap 808A of the closure and a portion of wall 816A of bell bag 800, with strip 820(1) closer to the opening of weight-receiving compartment 804 having a longitudinal axis 824(1) extending parallel to the most proximate side of the opening and strip 820(2) farther from the opening having a longitudinal axis 824(2) oriented perpendicular to longitudinal axis 824(1). This arrangement, or similar generally T-shaped arrangement, provides a firm seal but allows a user to disengage flap 808A with relatively little effort. In some embodiments, strip 820(2) may be narrower than strip 820(1) to provide even less resistance to a user opening flap 816A. Handle 812 may be padded but firm to provide comfort and robustness.

Bell bag 800 may be made of any suitable shell material(s), such as nylon, rayon, polyester or any other synthetic fiber, and/or natural fibers such as wool, silk, cotton, hemp, leather or any other natural fiber, and may include stiffening and/or padding components, such as polystyrene and padding. The shell can be made of a fast fiber that has no pliability or pliable or stretchy like lycra, elastine, elastic, neoprene, and any combination thereof. While closure 808 is illustrated as being secured using hook-and-loop fasteners, it can be secured by other means, such as one or more zippers, buttons, loops, strings over a button-like protrusion, snaps, hooks, buckles, magnetic strips or other magnetic means, laces, synching cord, clasps, clamps, or any combination of any of these means. In addition, while closure 808 is illustrated as being located on one side of bell bag 800, it can be located elsewhere, such as another side, top, bottom, along an edge, or at a corner, among others. Handle 812 and/or any number of handles can also be located on any side, top, bottom, or any corner of bell bag 800 and can be any size, shape, width, and diameter and can be made of any suitable material(s) such as polystyrene, wood, metal, polymer, plastic, leather, fiber glass, rubber, bone or any other suitable material, and any combination thereof. Handle 812 may be curved or straight, hollow or solid, among other things and combinations thereof. Handle 812 may be adjustable, detachable, fastened by stitching, glue, or attachable via buckle hook or any other system, including those listed above for components of other accessories. Bell bag 800 may have any number of attachments, such as pockets, scales or other weighing devices, coverings, wheels, straps, bungees, designs, markings, notepads, electronic devices, coatings, batteries, weights, buttons hooks, or other fasteners. Bell bag 800 can be any suitable size, shape, and weight, and can include any number of parts and components.

Figure 9A:
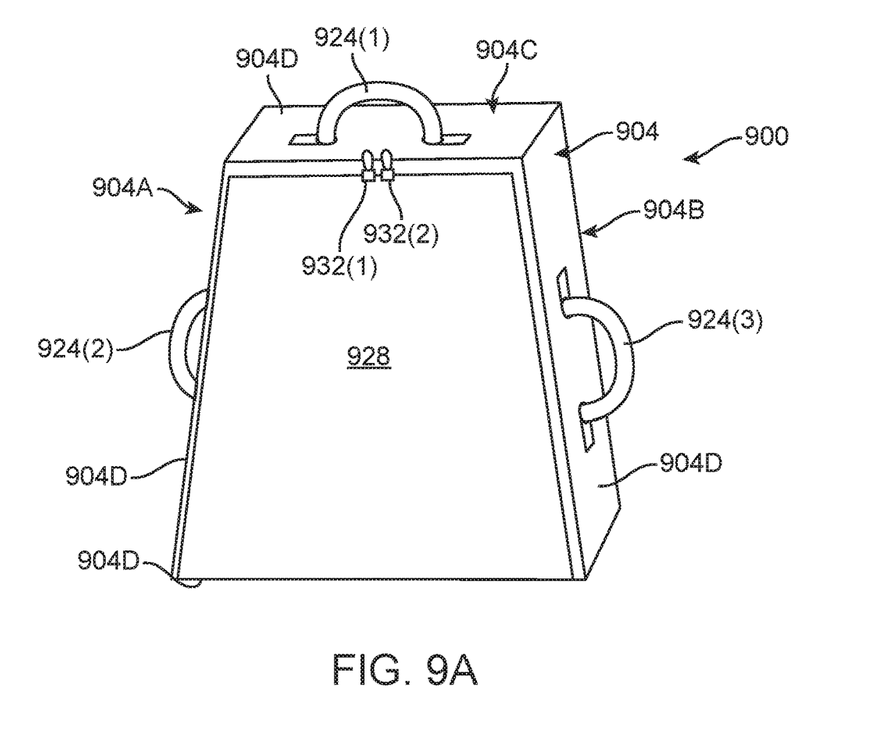
FIGS. 9A to 9C are various external views of an exemplary multifunctional rucksack that may be used to hold a plurality of discrete weights, bell bags, accessories, and other items and to be used as an exercise device.
Figure 9B:
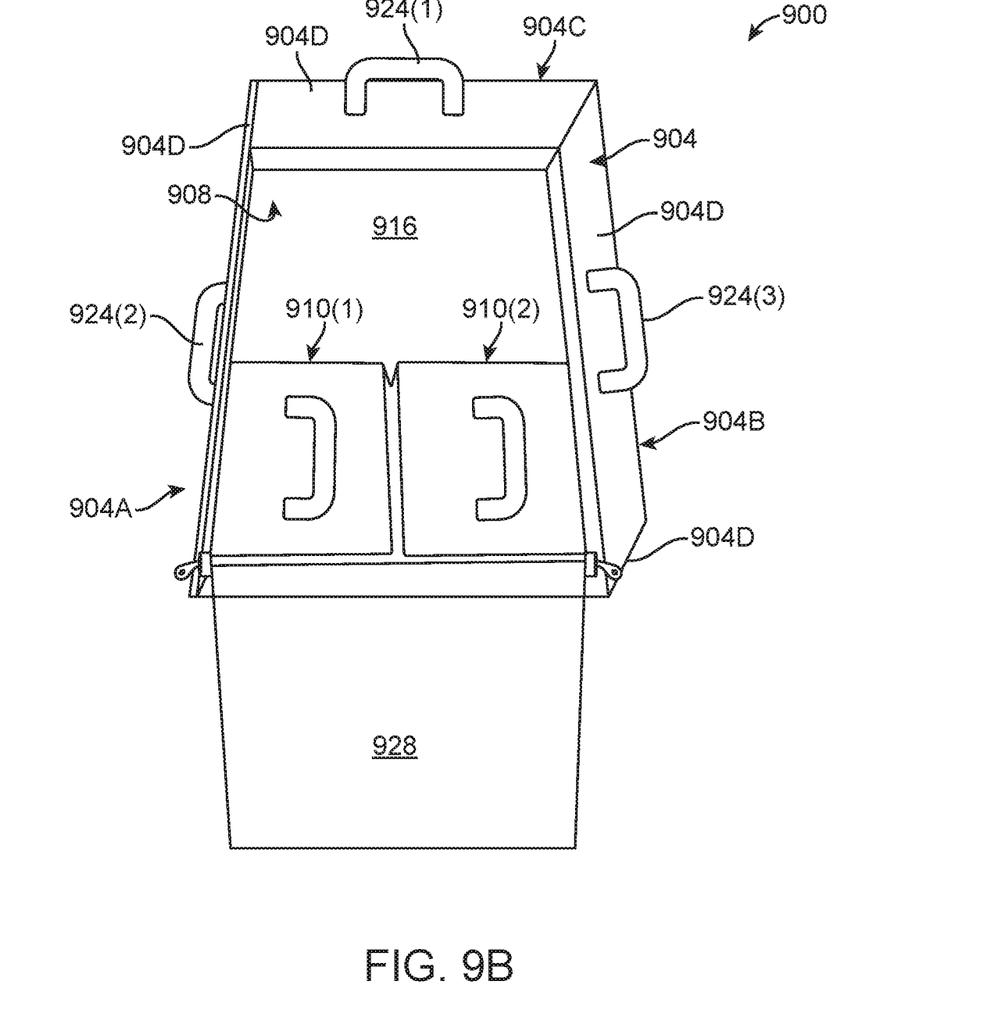
Figure 9C:
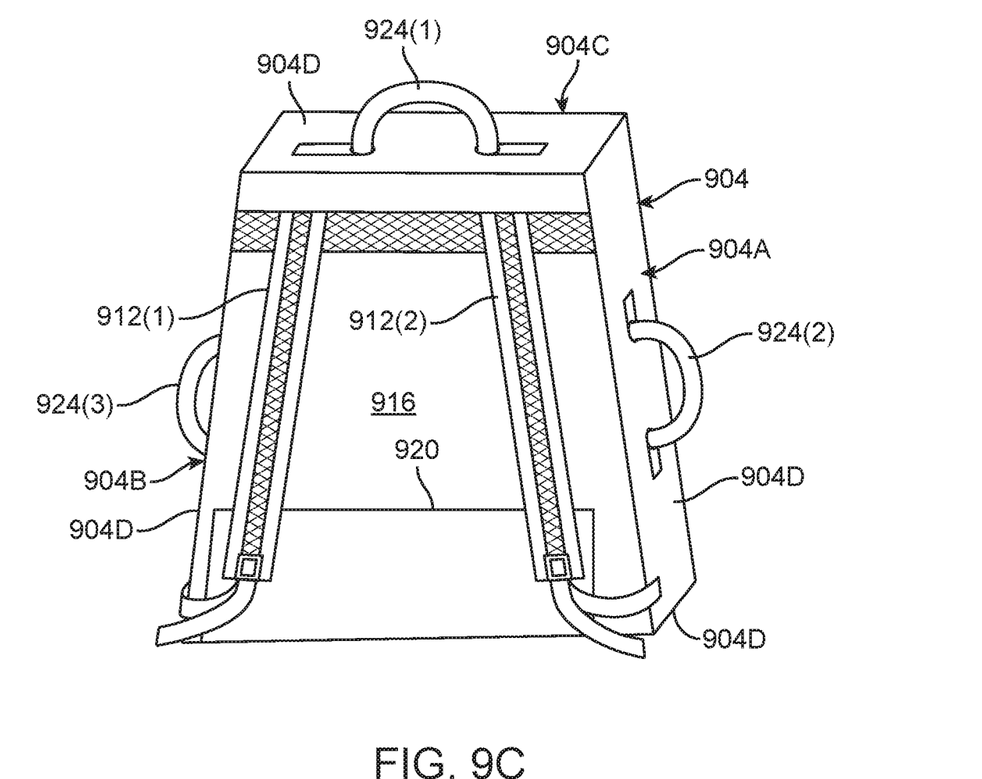

FIGS. 9A to 9C illustrate an exemplary accessory rucksack 900 that can be used with weights, such as weight pods, weight clusters, and/or bell bags, described above, among others, for example to carry the weights to a workout location and/or as an exercise device, such as a replacement for sandbag-type exercise devices, among other things. In this embodiment, rucksack 900 includes a main body 904 defining at least one weight-receiving compartment 908 (FIG. 9B) for receiving and containing weights during use. In one example, compartment 908 is designed and configured as a function of bell-bags, such as multiple ones of bell bag 800 of FIG. 8 (here two bell bags 910(1) and 910(2) are shown in FIG. 9B), so that multiple bell bags fit snugly within the weight-receiving compartment at least in two dimensions, for example, width and depth or width, depth, and height, so that the bell bags remain substantially in place during use. In some embodiments, the bell bags and corresponding interior surfaces of weight-receiving compartment 908 may include complementary components of suitable fasteners, such as hook-and-loop and/or interlocking-island fasteners, to help stabilize the bell bags during use. Weight-receiving compartment 908 may also be used by a user to store and/or carry not only weights, but also other accessories, such as bell bags and one or more straps, as well as other items, such as towels, clothing, and shoes, among many other types of items people typically put into rucksacks and gym bags.

Rucksack 900 includes a pair of shoulder straps 912(1) and 912(2) (FIG. 9C) to allow a user to carry the rucksack on their back in a manner similar to conventional rucksacks and backpacks. Shoulder straps 912(1) and 912(2) may be of the conventional padded type and optionally include a central chest strap and connector arrangement (not shown) that allows a wearer to connect the shoulder straps together at the user's chest for additional stability of rucksack 900 while being worn by the user, especially during vigorous movements, such as jogging, etc. In addition and in this connection, rucksack 900 may also include a waist strap (not shown, but see belt 700 of FIG. 7) that a wearer can use to stabilize the rucksack. Such a waist strap can be fixedly or removably secured to main body 904. In the embodiment shown, a back panel 916 of rucksack 900 includes a sleeve 920 (FIG. 9C) that receives belt 700 of FIG. 7 when the belt is being used as a waist strap.

In the embodiment shown, rucksack 900 includes three handles 924(1) to 924(3) to give a user multiple options for gripping the rucksack, for example, for using the rucksack for exercising as a weight or for orienting the rucksack for use as an exercise bench (see below) if the rucksack is so configured. In this example, handles 924(2) and 924(3) are located on opposing lateral sides 904A and 904B of main body 904, and handle 924(1) is located on the upper end 904C of the main body. It is noted that the relative terms used relative to rucksack 900 assume the rucksack is oriented as it would be when worn on the back of a user when the user is standing fully upright. Handles 924(1) to 924(3) allow the user to hold rucksack 900 single- or two-handedly, for example, for performing any suitable lifting exercise, such as a sandbag or medicine-ball exercise, among other things, such as functioning as a punching/kicking bag with one user holding the rucksack while another punches and/or kicks the rucksack. More or fewer handles can be provided, and/or handles can be provided at locations other than the locations shown to suit a particular design. Each handle is typically robust in size and construction in a manner similar to handle 812 of bell bag 800 of FIG. 8.

In the present embodiment, rucksack 900 is particularly designed and configured so that it can function as an exercise bench that can support a user in a supine orientation with the user's back supported on back panel 916 of main body 904. When rucksack 900 supports a user in this manner, the user can perform exercises common to exercise benches, such as butterfly and bench press exercises that work the user's arm and upper body muscles. To enable this functionality, walls 904D and back panel 916 of main body 904 are reinforced with stiffeners (not shown), such as rigid struts (e.g., aluminum, plastic, carbon fiber, etc.) and/or rigid panels (e.g., corrugated or honeycombed plastic or composite) that are robust enough to support at least the upper body of a user of a design size and a design amount of addition weight being lifted by the user, along with a suitable factor of safety.

In the embodiment shown, rucksack 900 includes a suitable closure, here a front panel 928 (FIG. 9A), which can be secured in a closed position using zippers 932(1) and 932(2) and/or any one or more suitable securing means, such as hook-and-loop fasteners, interlocking-island fasteners, buttons, loops, strings over a button-like protrusion, snaps, hooks, buckles, magnetic strips or other magnetic means, laces, synching cord, clasps, clamps, or any combination of any of these means. While the closure is illustrated as being located on the front side of rucksack 900, it can be located elsewhere, such as another side, upper end, bottom, back, along an edge, or at a corner, among others. Components of rucksack 900 can be made of, for example, nylon, polyester, or any other synthetic fiber or natural fiber such as cotton, hemp, wool or other suitable material. Main body 904 can be any size, shape dimension, with or without pockets, outside compartment, and/or attachments such as straps, bars, wheels, frames, etc. Rucksack 900 can have any number of electronic or non-electronic attachments for measuring weight or body functions such as heart rate, heart rate variability, metabolic rate, time, distance, calories burned, or whatever else may be of interest or import. Additional features that the rucksack can contain is a scale for weighing the total contents, a hands-free water bladder with mouth-tube for long hikes, and hook-and-loop straps to keep bags from sliding on a weight lifting bar.

Benefits of an exercise system of the present disclosure include one or more of the following, among others. Virtually all current modular systems require a bar or handle to attach weights to and, to the inventor's knowledge, no one has put the combination of soft and modular together in a convenient way that enables new exercises to be safely executed around the head area or convenient when combined with other fitness machines, such as the jogging machines or the wobble machines found in many gyms. There have been soft weighted balls with a thick rubber-like polymer given to patients by physical therapists for use mainly in the rehabilitation sector; however, these are not modular and not designed and made of materials that encourage combining to form heavier units.

A main technical problem with current systems is that they are typically not designed to be easily portable; they all require handles or bars to use in a modular way. Systems that are modular are not soft, and the current systems are less efficient regarding space they occupy and are not as comprehensive in applicability.

Another inherent problem for gyms is that people often want to use the same weight at the same time. This means either people must wait for that particular weight to become available or the gym must purchase multiple sets of dumbbells and kettlebells to meet demand. This is costly and inevitably, the problem still occurs because it is hard to foresee which weights will be needed. There are also some doubled weights that are rarely used and take up valuable space in a gym.

Another time where the use of weights is inefficient and dangerous is during group aerobic classes. Many aerobic routines use punching motions in the routine. Extra weights can be helpful to simulate using boxing gloves. In other classes with 20 to 30 or more people, it is very difficult to use large, bulky props that participants put at one's feet until they are needed. It is also dangerous when jumping around with hard dumbbells and bars of weights at one's feet, and it takes costly amounts of time to set up for and change weights for such a class. They also take up a huge amount of space to store all these.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An exercise system, comprising:
   a plurality of self-coupling weight pods designed and configured to form a weight cluster of known mass, each self-coupling weight pod:
   having a calibrated mass selected to contribute to the known mass of the weight cluster;
   including at least one magnet located on the self-coupling weight pod to allow the self-coupling weight pod to be magnetically coupled to at least one other one of the plurality of self-coupling weight pods to form the weight cluster;
   including a shell made of non-ferromagnetic material, the shell providing a chamber and a flexible envelope having an exterior surface; and
   including a ferromagnetic material contained within the chamber;
   wherein:
   the shell includes a flexible outer layer;
   the shell further includes a flexible inner layer that contains the ferromagnetic material within the chamber; and
   the at least one magnet is located externally to the inner layer.

2. The exercise system according to claim 1, further comprising a rucksack designed and configured to allow a user to lift or carry at least the weight cluster, the rucksack comprising:
   a weight-cluster compartment designed and configured to securely contain at least the weight cluster;
   a pair of shoulder straps designed, configured, and located on the rucksack to allow the user to carry the rucksack as a backpack; and
   a plurality of handles designed, configured, and located to allow the user to lift the rucksack in a plurality of differing manners.

3. The exercise system according to claim 2, wherein two handles of the plurality of handles are located at opposing lateral sides of the rucksack so as to allow the user to lift the rucksack with two hands with each hand engaging a corresponding one of the two handles.

4. The exercise system according to claim 3, further comprising a third handle located on an exterior surface of the rucksack between the opposing lateral sides.

5. The exercise system according to claim 2, wherein the weight-cluster compartment is sized and configured to snugly receive a plurality of like-size bell bags.

6. The exercise system according to claim 2, wherein the rucksack includes a back panel and side walls, wherein the back panel and side walls are designed and configured, and the rucksack is sized, to function as a weight bench and support the user when the user is in a supine position with the torso of the user supported on the back panel of the rucksack.

7. The exercise system according to claim 2, wherein the rucksack further comprises a removable waist strap for stabilizing the rucksack when the rucksack is worn on the back of the user, wherein the removable waist strap is designed and configured to:
   be worn by the user as a weight belt; and
   support a plurality of the self-coupling weight pods during use of the removable waist strap as a weight belt.

8. The exercise system according to claim 1, wherein the ferromagnetic material comprises a mass of flowable ferromagnetic material.

9. The exercise system according to claim 8, wherein the flowable ferromagnetic material comprises metal balls.

10. The exercise system according to claim 8, wherein each self-coupling weight pod comprises a flexible shell that contains the mass of flowable ferromagnetic material and that elastically deforms when magnetically clamped between the magnet of another of the plurality of self-coupling weight pods and the mass of flowable magnetic material.

11. The exercise system according to claim 1, further comprising a strap designed and configured to be fastened around a body part of a user, the strap including a coupling feature for securing one or more of the plurality of self-coupling weight pods to the strap.

12. The exercise system according to claim 11, wherein the at least one coupling feature of the strap comprises a holster.

13. The exercise system according to claim 11, wherein the strap is designed and configured to be secured around a limb of the user.

14. The exercise system according to claim 1, wherein each self-coupling weight pod includes at least two magnets located to allow the self-coupling weight pod to be magnetically coupled to at least two other ones of the plurality of self-coupling weight pods to form the weight cluster.

15. The exercise system according to claim 1, wherein differing ones of the plurality of self-coupling weight pods have differing calibrated masses.

16. The exercise system according to claim 1, further comprising a bell bag designed and configured to allow a user to use the weight cluster as an exercise kettlebell, the bell bag comprising:
   a weight-cluster compartment designed and configured to securely contain the weight cluster; and
   a handle designed, configured, and located on the bell bag to allow the user to hold the bell bag in a manner the user would hold an exercise kettlebell.

17. An exercise device, comprising:
   a shell made of non-ferromagnetic material, the shell providing a chamber and having an exterior surface;
   a ferromagnetic material contained within the chamber; and
   at least one magnet located on the exercise device so as to attract the exercise device to a ferromagnetic body located externally to the exercise device;
   wherein:
      the shell includes a flexible outer layer;
      the shell further includes a flexible inner layer that contains the ferromagnetic material within the chamber; and
      the at least one magnet is located externally to the inner layer.

18. The exercise device according to claim 17, wherein the shell is substantially spherical when not under the influence of any external forces.

19. The exercise device according to claim 18, wherein the shell has an external diameter of about 1 inch (~2.54 cm) to about 4 inches (~10.2 cm).

20. The exercise device according to claim 17, wherein each of the at least one magnet has a magnetic axis extending between north and south poles and the magnetic axis is oriented so that only one or the other of the north and south poles faces externally to the shell.

21. The exercise device according to claim 20, wherein the shell has a spherical shape when not under the influence of any external loads and the magnetic axis is oriented radially relative to the spherical shape.

22. The exercise device according to claim 17, wherein the at least one magnet extends into the flexible outer layer.

23. The exercise device according to claim 17, wherein the ferromagnetic material has a weight in a range of about 0.5 kg to about 2 kg.

24. The exercise device according to claim 17, wherein the ferromagnetic material comprises ferromagnetic spheres each having a diameter less than about 0.25 inch (~0.64 cm).

* * * * *